United States Patent [19]

Dulog et al.

[11] 3,962,201

[45] June 8, 1976

[54] PROCESS FOR POLYMERIZING ACRYLICS EMPLOYING (HYDROCARBON-PEROXY HYDROCARBON) PHOSPHONATES

[75] Inventors: Lothar G. Dulog, St. Martens-Latem; Willy P. Broeckx, Reet, both of Belgium

[73] Assignee: S. A. Texaco Belgium N.V., Brussels, Belgium

[22] Filed: Nov. 21, 1974

[21] Appl. No.: 526,018

Related U.S. Application Data

[62] Division of Ser. No. 415,025, Nov. 12, 1973, which is a division of Ser. No. 291,898, Sept. 25, 1972.

[52] U.S. Cl. .............................. 526/193; 526/217; 526/227; 526/328; 526/341
[51] Int. Cl.² ............... C08F 220/42; C08F 220/70; C08F 120/42; C08F 120/70
[58] Field of Search ......... 260/85.5 F, 80 C, 89.5 R, 260/89.5 A, 88.7 D, 88.1 P, 85.7, 92.8, 94.2 R, 94.6

[56] References Cited

UNITED STATES PATENTS

| | | | |
|---|---|---|---|
| 3,285,994 | 11/1966 | Leithauser | 260/88.7 D X |
| 3,324,200 | 6/1967 | Leithauser | 260/85.5 D X |
| 3,326,859 | 6/1967 | Seiner | 260/85.5 F X |

*Primary Examiner*—Joseph L. Schofer
*Assistant Examiner*—Herbert J. Lilling
*Attorney, Agent, or Firm*—T. H. Whaley; C. G. Ries; Carl G. Seutter

[57] ABSTRACT

(Hydrocarbon-peroxy hydrocarbon) phosphonates, useful as polymerization initiators, prepared by the reaction of a hydroperoxide with a phosphonate of an unsaturated hydrocarbon may be used to polymerize acrylic monomers.

7 Claims, No Drawings

PROCESS FOR POLYMERIZING ACRYLICS EMPLOYING (HYDROCARBON-PEROXY HYDROCARBON) PHOSPHONATES

This application is a divisional application of U.S. Ser. No. 415,025, filed Nov. 12, 1973 for Process for Polymerizing which application is a divisional application of U.S. Ser. No. 291,898, filed Sept. 25, 1972 for Preparation of (Hydrocarbon-peroxy Hydrocarbon) Phosphonates.

BACKGROUND OF THE INVENTION

As is well known to those skilled in the art, a wide variety of phosphorus-containing compounds has heretofore been prepared by various processes. It has not however heretofore been possible to prepare (hydrocarbon peroxy hydrocarbon) phosphonates.

It is an object of this invention to provide a process for preparing product (hydrocarbon peroxy hydrocarbon) phosphonates. It is another object of this invention to provide novel products including (alkylperoxy hydrocarbon) phosphonates which may find a wide variety of uses, including use as polymerization initiator. Other objects will be apparent to those skilled in the art.

STATEMENT OF THE INVENTION

In accordance with certain of its aspects, the novel process of this invention for polymerizing an acrylic may comprise initiating said polymerization in the presence of a (hydrocarbon peroxy hydrocarbon) phosphonate

(I)

R'' is divalent hydrocarbon, and X is —OR or —NR$_2$ thereby forming said product polymer; and recovering said product polymer.

DESCRIPTION OF THE INVENTION

The charge phosphonate of an unsaturated hydrocarbon, typically an alkenyl phosphonate, which may be employed in practice of this invention may be a compound having the formula:

(II)

wherein R' is a divalent ethylenically unsaturated moiety having an alpha-hydrogen atom. The double bond of the R' group is attached to the alpha-carbon i.e. the carbon atom attached to the phosphorous atom. It will be apparent that —R'H may thus be an alkenyl group, and preferably an alpha-alkenyl or 1-alkenyl group. The —R'H group may be a hydrocarbon group containing adjoining ethylenically unsaturated carbon atoms, i.e. carbon atoms having an ethylenically active double bond therebetween. Typical of the —R'H groups may be alkenyl groups including aralkenyl, and such groups when inertly substituted. When —R'H is alkenyl it may typically be vinyl or 2-substituted vinyl such as 1-propenyl, 1-butenyl, 1-pentenyl, etc. When —R'H is aralkenyl, it may typically be 2-phenyl-ethenyl, 3-phenyl-1-propenyl, 4-tolyl-1-butenyl, etc. —R'H may be inertly substituted i.e. it may bear a non-reactive substituent such as alkyl, aryl, cycloalkyl, ether, halogen, etc. Typically inertly substituted —R'H groups may include 3-chloropropenyl 2-ethoxyethenyl, carboethoxyethenyl, p-chlorophenethenyl, etc. The preferred — R'H groups may be lower alkenyl, i.e. C$_2$–C$_{10}$ alkenyl groups including eg vinyl, 1-propenyl, 1-butenyl, etc.

It will be apparent to those skilled in the art that when a given formula or equation includes more than one group designated by the same symbol (eg R, R', R'', X, etc.), they need not be the same. Thus in formula II, supra one X might be ethoxy and one X might be methoxy.

The preferred —R'H groups may be the alken-1-yl i.e. alkenyl groups wherein the double bond is present on the alpha or first carbon. Typical of these groups may be vinyl, which is preferred. When R'H is vinyl, the compound may be a vinyl phosphonate. It will be clear from inspection that the R' unsaturated group of the charge compound may be converted to the divalent R'' group in the product.

In the charge phosphonate, the X group may be —OR or —NR$_2$. R may be a hydrocarbon radical selected from the group consisting of alkyl, aralkyl, cycloalkyl, aryl, alkaryl, alkenyl, and alkynyl (with the unsaturated bonds not alpha to oxygen or nitrogen) including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenyl-ethyl, etc. When R is cycloalkyl, it may typically be cyclohexyl, cycloheptyl cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. When R is alkenyl (with the unsaturated bond not alpha to oxygen or nitrogen) it may typically be 1-propenyl, 1-butenyl, etc. When R is alkynyl (with the triple bond not alpha to oxygen or nitrogen), it may typically be 1-propynyl, 1-butynyl, etc. R may be inertly substituted i.e. it may bear a non-reactive substituent such as alkyl, aryl, cycloalkyl, ether, halogen, nitro, etc. Typically inertly substituted R groups may include 3-chloropropyl, 2-ethoxyethyl, carboethoxymethyl, 4-methyl cyclohexyl, p-chlorophenyl, p-chlorobenzyl, 3-chloro-5-methylphenyl, etc. The preferred R groups may be lower alkyl, i.e. C$_1$–C$_{10}$ alkyl, groups including e.g. methyl, ethyl, n-propyl, i-propyl, butyls, amyls, hexyls, octyls, decyls, etc. R may preferably be a tertiary hydrocarbon, most preferably t-butyl, cumyl (i.e. 2-phenylisopropyl), etc.

In the charge phosphonate, X may be —NR$_2$, a disubstituted amine group or —OR, an alkoxy (including aryloxy etc.) group.

Illustrative of the X groups when X is —OR may be methoxy, ethoxy, phenoxy, n-butoxy, and cyclohexyloxy; illustrative of the X groups, when X is —NR$_2$, may be di-ethylamino, dimethylamino, etc.

It will be apparent to those skilled in the art, that the charge phosphonate may be an ester type, an amide type, or an ester-amide type (the latter sometimes being referred to as an estamide) depending on whether both X groups are —OR or —NR$_2$ or whether one X group is —OR and the other —NR$_2$.

In the preferred embodiment, the charge phosphonate will be an ester type; and it may have the formula (III).

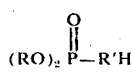
$$(RO)_2\overset{\overset{O}{\|}}{P}-R'H \qquad (III)$$

Typical of the charge phosphonates which may be employed in practice of this invention, may be those set forth in the following table.

TABLE I dimethyl vinylphosphonate
di-n-propyl vinylphosphonate
dicyclohexyl vinylphosphonate
N,N,N',N'-tetraethyl diamidovinylphosphonate
N,N,N',N'-tetramethyl diamidobuten-1-ylphosphonate
diethyl vinylphosphonate
di-n-butyl vinylphosphonate
methyl-N,N'-dimethyl amidovinylphosphonate
ethyl-N,N-'dimethyl amidovinylphosphonate
N,N,N',N'-tetramethyl diamidovinylphosphonate
N,N',-tetra-n-butyl diamidovinylphosphonate The above charge phosphonates may be readily available or they may be prepared as desired. The preferred charge phosphonates may be those where R'H is vinyl and X$_2$ is (OR)$_2$. More specifically the preferred phosphonates may be di(lower alkyl) vinylphosphonates, most preferably dimethyl vinylphosphonate, diethyl vinylphosphonate, and di-n-butyl vinylphosphonate.

The hydroperoxide R—O—O—H which may be used as charge to the process of this invention may be a hydroperoxide wherein R is hydrocarbon. The preferred hydroperoxide may be a tertiary alkyl hydroperoxide, (and preferably a C$_1$ to C$_{10}$ lower alkylhydrogenperoxide) such as t-butyl hydroperoxide or cumylhydroperoxide.

In accordance with a preferred embodiment of this invention, it may be desirable to use as the charge peroxide, a mixture of the peroxide se and the alkali metal salt of the peroxide. Typically the charge peroxide composition may be employed in the form of a mixture containing 3–20 parts, preferably 5–10 parts, say 7.5 parts of the peroxide se, typically t-butylhydroperoxide, and 0.5–5 parts, preferably 0.5–3, say 1 part of an alkali metal salt thereof e.g. the sodium salt of t-butylhydroperoxide. Preferably the salt used will be a salt of the same peroxide which is also present in free form.

In carrying out the process of this invention in accordance with certain of its aspects, 3–20 parts, preferably 5–10 parts, say 7.5 parts of the peroxide ROOH may be added to the reaction medium together with 1–5 parts, preferably 2–4 parts, say 3 parts of the charge phosphonate. Preferably the amount of peroxide added to the reaction medium may be 100–1000%, preferably 250–750%, say 500% of the equivalent amount required to react with the phosphonate according to the following reaction:

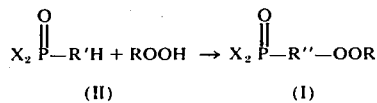
$$X_2\overset{\overset{O}{\|}}{P}-R'H + ROOH \rightarrow X_2\overset{\overset{O}{\|}}{P}-R''-OOR$$
$$(II) \qquad\qquad (I)$$

A typical specific reaction which may be carried out by the process of this invention may be the following:

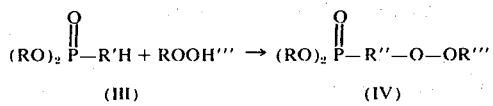
$$(RO)_2\overset{\overset{O}{\|}}{P}-R'H + ROOH''' \rightarrow (RO)_2\overset{\overset{O}{\|}}{P}-R''-O-OR'''$$
$$(III) \qquad\qquad (IV)$$

Reaction may be carried out at 20°C–100°C, preferably 20°C–40°C, say 25°C at pressure of 0–1000 p.s.i.g., preferably 0–20 p.s.i.g., say atmospheric pressure. The reaction may be exothermic; and accordingly provision for cooling and agitation may be provided.

If desired, the reaction may be carried out in the presence of inert diluent-solvent such as dioxane, or particularly solvent systems such as the mixtures: water-tetrachloroethylene or water-dioxane. More preferably, however, the reaction may be carried out either in the absence of diluent-solvent or with the t-alkyl-hydroperoxide itself as the diluent.

The reaction is preferably carried out in the presence of catalyst in the preferred embodiment. The preferred catalyst may be a basic catalyst, typified by alkali metal salts of hydroperoxides, alkali metal alkoxides, or alkali metal hydroxides. When the alkali metal salt is a salt of a hydroperoxide, it is preferred that the hydroperoxide be the same hydroperoxide as that participating in the reaction. Typical of such basic catalyst may be the sodium salt of t-butylhydroperoxide. When the base catalyst is an alkali metal alkoxide, it may commonly be an alkali metal alkoxide of a lower alkyl (C$_1$–C$_{10}$) alcohol. Typical of the alkoxides which may be employed as catalysts may be sodium methoxide, potassium t-butoxide, sodium ethoxide, and lithium ethoxide. A typical alkali metal hydroxide may be sodium hydroxide. The preferred catalyst may be the sodium salt of t-butylhydroperoxide.

During the course of the reaction which may occur over 60–200 minutes, preferably 100–150 minutes, say 120 minutes, the reaction may be controlled by cooling. At the conclusion of the reaction as typically observed by the absence of continuing exotherm, inert hydrocarbon diluent-solvent (in which the catalyst is insoluble) may be added to the reaction mixture. Typical of the inert hydrocarbon liquids which may be added as diluent-solvent may be pentane, hexane, heptane, octane etc., preferably pentane. The inert diluent-solvent may precipitate the base catalyst present in the reaction medium. The precipitated base catalyst may then be filtered off.

The added diluent-solvent, unreacted hydroperoxide, and unreacted vinyl phosphonate may be distilled off at pressure of 1–20 mm. Hg, preferably 10–18 mm. Hg, say 14 mm. Hg. The product phosphonate, obtained in yields up to 65 percent may be purified by column chrommatography using silica gel as adsorbing phase and chloroform as eluent, or alternatively, may be used as is in crude state. In the preferred embodiment, the reaction may be carried out in substantially anhydrous reaction medium.

The novel products which may be prepared in accordance with the process of this invention may typically be found to be high boiling liquids. Illustrative specific products may be those set forth in the following table.

TABLE dimethyl t-butylperoxyethylphosphonate diethyl t-butylperoxyethylphosphonate
dipropyl t-butylperoxyethylphonphonate
di-n-butyl t-butylperoxyethylphosphonate
diphenyl t-butylperoxyethylphosphonate
dimethyl cumylperoxyethylphosphonate
diethyl cumylperoxyethylphosphonate
diphenyl cumylperoxyethylphosphonate
N,N,N',N'-tetramethyl diamido-2-(t-butylperoxy)-ethylphosphonate
N,N,N',N'-tetramethyl diamido-2-(cumylperoxy)-ethylphosphonate
N,N,N',N'-tetramethyl diamido-2-(cumylperoxy)-ethylphosphonate
methyl N,N diethyl amido-2-(t-butylperoxy)-ethylphosphonate
di-methyl t-butylperoxyethylphosphonate
dimethyl pinaneperoxyethylphosphonate The novel products prepared in accordance with the process of this invention may be found to be useful for a wide variety of uses. Typically, for example, they may be found to be useful as polymerization initiators for the quantitative polymerization of polymers by radical polymerization reactions. Typical of such polymers, the polymerization of which may be initiated by these novel products, may be noted polymers of vinyl-type prepared from eg ethylene, vinyl acetate, vinyl chloride, styrene, butadiene etc. and more particularly acrylic-type polymers prepared from monomers such as acrylonitrile, methyl methacrylate, methyl acrylate, etc.

Polymerization of polymers such as acrylics may be effected by the use of these initiators by adding 0.01–1 parts, preferably 0.01–0.1 parts, say 0.05 parts of the desired polymerization initiator per 100 parts of monomer. The desired polymerization initiator may be dimethyl t-butyl-peroxyethanephosphonate, diethyl cumylperoxyethanephosphonate, diphenyl t-butyl-peroxyethanephosphonate, N,N,N',N'-tetramethyl diamido-2-(2-t-butyl) ethylphosphonate. Typically, 0.01–1 parts, preferably 0.01–0.1 parts, say 0.05 parts of dimethyl t-butylperoxyethanephosphonate may be added to 100 parts of e.g. acrylonitrile optionally dissolved in toluene inert diluent.

Reaction mixture may be maintained at 60°C and 14.7 psig for 18 hours during which time polymerization may be effected. At the end of this reaction time, the desired product polyacrylonitrile may be worked up by filtration of the polyacrylonitrile and washing with 500 parts of n-pentane. A control reaction without the dimethyl-t-butyl peroxyethane phosphonate gave under the same conditions no polyacrylonitrile.

These novel compositions may also be useful as flameproofing agents, when incorporated in plastics (eg polyvinylchloride) in amount of 0.01–5 parts, preferably 0.001–1 parts, say 0.15 parts per 100 parts of plastic. It may be noted when these compositions are used as initiating agents to polymerize monomers, the final product polymer may have incorporated therein chemically bound fragments of the initiator; and these fragments may impart flame-proofing properties to the polymer product.

It is also a novel feature of the products of this invention that they may readily catalyze the reaction of hydrocarbons to permit production of dimers or oligomers. Typically, for example, cyclohexane may be dimerized or oligomerized to form dicyclohexane by dimerization in the presence of dimethyl t-butylperoxyphosphonate as catalyst.

It will be apparent to those skilled in the art that the novel (hydrocarbonperoxy) phosphonate products prepared by the process of this invention may be highly active. Accordingly, it may be desirable to store them under conditions conducive to maintaining the integrity of the product. Preferably, these products may be stored under anhydrous conditions and free of any impurities which may assist or participate in the decomposition. They are stable at room temperature; preferably they may be stored in a closed opaque vessel.

DESCRIPTION OF PREFERRED EMBODIMENTS

Practice of the process of this invention may be observed from the following illustrative examples wherein, as elsewhere in this specification, all parts are parts by weight unless otherwise noted

EXAMPLE I

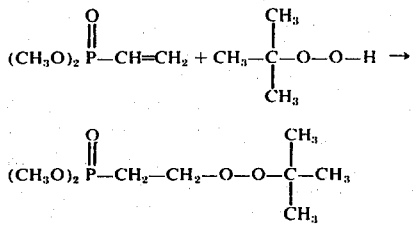

In this example which represents practice of a preferred embodiment of this invention, 2.7 parts (0.025 moles) of dimethyl vinylphosphonate and a solution of 1 part (0.009 moles) of the sodium salt of t-butylhydroperoxide in 7.5 parts (0.069 moles) of t-butylhydroperoxide may be added to a reaction medium with stirring. As the exothermic reaction occurs, the temperature may increase from the initial temperature of 25°C up to a final temperature of 65°C. Thereafter, as reaction occurs further, temperature may drop to 25°C. At this point, 100 parts of n-pentane may be added and a precipitate of catalyst sodium t-butylhydroperoxide may be noted. The precipitate may be filtered, and the filtrate distilled to remove as distillate 100 parts of n-pentane, 4.8 parts of t-butylhydroperoxide, and 0.9 parts dimethyl vinylphosphonate. 3 parts (0.013 moles) of desired product dimethyl t-butylperoxyethanephosphonate may be obtained as slightly yellow oil in yield of 65 percent (based on dimethyl vinylphosphonate). Elemental analysis indicated H:calc 8.39%, found 8.07%; P: calc 13.70%, found 13.80%.

EXAMPLE II

In this example, 4 parts (0.029 moles) of dimethyl vinylphosphonate and a solution of 0.6 parts (0.005 moles) of potassium t-butylate in 7.3 parts (0.081 moles) of t-butylhydroperoxide may be added with stirring to a reaction mixture. The strong exothermic reaction may increase the temperature from an initial 25°C. to a final 65°C. at which latter temperature, the reaction mixture may be maintained during the course of reaction. At the conclusion of the reaction, the reaction mixture may be worked up in a manner comparable to that of Example I. Dimethyl t-butylperoxyethanephosphonate may be obtained in amount of 4 parts (61% yield).

EXAMPLE III

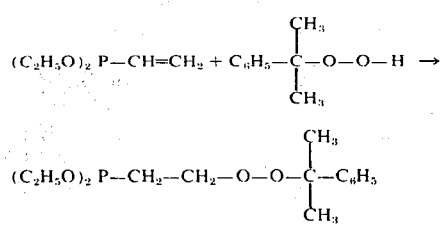

Four parts (0.024 moles) of diethyl vinylphosphonate and a solution of 0.6 parts (0.005 moles) of potassium t-butylate in 17.5 parts (0.081 moles) of cumyl hydroperoxide (70%) may be added to a reaction mixture. As reaction progresses, the temperature may increase from 25°C. up to 55°C. After 60 minutes, the reaction may be completed and the temperature of the reaction mixture may drop again to 25°C. At this time, 200 parts of n-pentane may be added to the reaction mixture to precipitate catalyst potassium t-butylate. The precipitated catalyst may be filtered off. The filtrate may then be distilled to recover as distillate, solvent and excess diethyl vinylphosphonate. The desired crude product, diethyl betacumylperoxyethanephosphonate may be further purified by preparative thin layer chromotography. A silica gel adsorbent is used with chloroform and 1% ethanol as mobile phase. The desired product obtained in the amount of 1 part (8% yield) may be isolated and upon analysis may be found to contain 8.11% hydrogen (calculated 7.99%) and 9.0% phosphorus (calculated 9.81%).

EXAMPLE IV

In this example which represents practice of a process carried out in accordance with this invention, 2.4 parts (0.04 moles) of acrylonitrile may be admitted to a sealed tube in the presence of 0.006 parts (0.00002 moles) of dimethyl t-butylperoxyethanephosphonate. The mixture may be degassed by passage therethrough of nitrogen, and the tube sealed and heated to 60°C. After 3 minutes, polymerization may start, as indicated by the precipitation of the polymer. After 18 hours, no further evidence of reaction may be noted. The contents of the sealed tube may be analyzed to show that the monomer had polymerized substantially quantitatively in the reaction period of 18 hours to yield poly(acrylonitrile).

A control reaction was carried out with no phosphates present; and it was found that no polymerization occurred in the absence of phosphate.

EXAMPLE V

0.538 parts (0.0024 moles) of dimethyl t-butylperoxyethanephosphonate and 8.9 parts (0.06 moles) of cyclohexane may be placed in a tube, and degassed with nitrogen. The tube may then be sealed and heated to 120°C. for 24 hours. At the end of this time, the reaction mixture may be extracted with cyclohexane and analysis of the cyclohexane-soluble fraction by gas chromatography may show the presence of bicyclohexane.

EXAMPLE VII

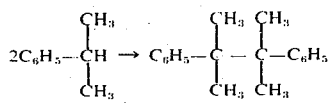

In this example, 0.538 parts (0.0024 moles) of dimethyl t-butylperoxethanephosphonate and 4.6 parts (0.038 moles) of cumene may be placed within a reaction vessel, degassed, and the reaction vessel sealed. After heating in the sealed tube for 16 hours at 120°C. the reaction mixture was homogeneous. Analysis of the cumene-soluble fraction shows the presence of dicumene.

It will be apparent to those skilled in the art that this invention has been described with respect to specific embodiments; and numerous changes and modification will be apparent which fall within the scope of this invention.

We claim:

1. The process for polymerizing an acrylic selected from the group consisting of acrylonitrile, and esters of acrylic acid and methacrylic acid which comprises initiating said polymerization reaction in the presence of

wherein R is a hydrocarbon containing less than about 18 carbon atoms and it may be inertly substituted, R'' is divalent hydrocarbon containing 2–10 carbon atoms and R'' may be inertly substituted, and X is —OR or NR$_2$ thereby forming polymer; and recovering said polymer.

2. The process for polymerizing an acrylic monomer selected from the group consisting of acrylonitrile, and esters of acrylic acid and methacrylic acid as claimed in claim 1 wherein said

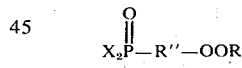

is present in amount of 0.01–0.1 parts per 100 parts of monomer.

3. The process for polymerizing an acrylic monomer selected from the group consisting of acrylonitrile, and esters of acrylic acid and methacrylic acid as claimed in claim 1 wherein said

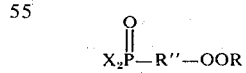

is

4. The process for polymerizing an acrylic monomer selected from the group consisting of acrylonitrile, and esters of acrylic acid and methacrylic acid as claimed in claim 1 wherein said

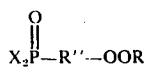

is selected from the group consisting of dimethyl t-butyl-peroxyethanephosphonate, diethyl cumyl-peroxy ethanephosphonate, diphenyl t-butyl-peroxyethanephosphonate, and N,N'-dimethyl diamido-2-(2-t-butyl-)ethylphosphonate.

5. The process for polymerizing acrylonitrile as claimed in claim 1 which comprises initiating said polymerization in the presence of 0.01–0.1 parts, per 100 parts of monomer, of composition selected from the group consisting of dimethyl t-butylperoxyethanephosphonate, diethyl cumyl-peroxy ethanephosphonate, diphenyl t-butyl-peroxyethanephosphonate, and N,N'-dimethyl diamido-2-t-butyl)ethylphosphonate.

6. The process for polymerizing acrylonitrile as claimed in claim 1 wherein said

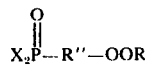

is present in amount of 0.01–0.1 parts per 100 parts of monomer.

7. The process for polymerizing acrylonitrile as claimed in claim 1 wherein said

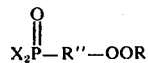

is selected from the group consisting of dimethyl t-butyl-peroxyethanephosphonate, diethyl cumyl-peroxy ethanephosphonate, diphenyl t-butyl-peroxyethanephosphonate, and N,N'-dimethyl diamido-2-(2-t-butyl-)ethylphosphonate.

* * * * *